US008465470B2

(12) United States Patent
Kipperman

(10) Patent No.: US 8,465,470 B2
(45) Date of Patent: Jun. 18, 2013

(54) PATENT FORAMEN OVALE CATHETER AND METHOD OF USING THE SAME

(76) Inventor: Robert Kipperman, Chatham, NJ (US)

( * ) Notice: Subject to any disclaimer, the term of this patent is extended or adjusted under 35 U.S.C. 154(b) by 347 days.

(21) Appl. No.: 12/843,273

(22) Filed: Jul. 26, 2010

(65) Prior Publication Data

US 2011/0022004 A1    Jan. 27, 2011

Related U.S. Application Data

(60) Provisional application No. 61/228,663, filed on Jul. 27, 2009.

(51) Int. Cl.
*A61M 25/00*    (2006.01)

(52) U.S. Cl.
USPC .......................................................... 604/532

(58) Field of Classification Search
USPC .......................................................... 604/532
See application file for complete search history.

(56) References Cited

U.S. PATENT DOCUMENTS

| | | | |
|---|---|---|---|
| 3,485,234 A | 12/1969 | Stevens | |
| 5,016,640 A | 5/1991 | Ruiz | |
| 5,215,540 A | 6/1993 | Anderhub | |
| 5,575,766 A | 11/1996 | Swartz et al. | |
| 5,814,028 A | 9/1998 | Swartz et al. | |
| 5,885,247 A | 3/1999 | Slagboom | |
| 5,891,057 A | 4/1999 | Chaisson et al. | |
| 6,004,280 A | 12/1999 | Buck et al. | |
| 6,650,923 B1 | 11/2003 | Lesh et al. | |
| 6,887,229 B1 | 5/2005 | Kurth | |
| 7,056,294 B2 | 6/2006 | Khairkhahan et al. | |
| 7,976,531 B2 * | 7/2011 | Johnson ........................ | 604/532 |
| 2008/0161777 A1 | 7/2008 | Kurth et al. | |
| 2009/0234300 A1 | 9/2009 | Osypka | |

FOREIGN PATENT DOCUMENTS

WO    2004087235 A2    10/2004

OTHER PUBLICATIONS

International Search Report and Written Opinion issued Oct. 1, 2010 in Int'l Application No. PCT/US2010/43212, 13 pages.
Mullins, Charles E., "Transseptal Left Heart Catheterization: Experience with a New Technique in 520 Pediatric and Adult Patients," Ped Cardiol, 4:239-246, 1983.

* cited by examiner

*Primary Examiner* — Theodore J Stigell
*Assistant Examiner* — Rebecca E Eisenberg
(74) *Attorney, Agent, or Firm* — Panitch Schwarze Belisario & Nadel LLP

(57) ABSTRACT

A catheter for use in accessing a left atrium of a living heart within a subject's body by passing from the heart's right atrium to the heart's left atrium through a patent foramen ovale (PFO) in the heart, such as performing a percutaneous procedure for closing the PFO, includes a specialized preformed catheter with curves on the distal portion to be adapted within living anatomy to allow access from a subject's heart's right atrium through the PFO to the left atrium. The catheter facilitates access to the left atrium and the use of devices in procedures within and involving the left atrium, such as PFO closure devices. A method is also provided for using the catheter.

25 Claims, 2 Drawing Sheets

PATENT FORAMEN OVALE CATHETER AND METHOD OF USING THE SAME

CROSS-REFERENCE TO RELATED APPLICATIONS

This application claims the benefit of U.S. Provisional Patent Application 61/228,663, filed Jul. 27, 2009, the disclosure of which is hereby incorporated by reference herein, in its entirety.

FIELD OF THE INVENTION

This invention generally relates to a catheter, and preferably, but not exclusively, a diagnostic catheter, which is suitable for being directed to or for directing a guide wire to the left atrium of the heart through a patent foramen ovale or for canulating the patent foramen ovale canal.

BACKGROUND OF THE INVENTION

The foramen ovale is the congenital communication between the right atrium and left atrium of a heart in utero, allowing oxygenated maternal blood to bypass the lungs of the fetus and go directly to the systemic circulation. It closes completely in the majority of people soon after birth. Studies suggest that there is incomplete closure, called a patent foramen ovale (PFO), in approximately 25 percent of the general population. There appears to be an increased rate of PFO in patients with cryptogenic stroke and migraines suggesting a casual relationship. Closure of a PFO appears to reduce the risk of recurrent stroke and possibly reduces the incidence of migraines. In the past, PFOs were closed surgically with an open chest procedure.

Later, PFOs have been closed in a percutaneous procedure using one of several devices that are considered by the U.S. Food and Drug Administration to be subject to an investigational device exemption (IDE), known as IDE devices. More recently, percutaneous closure of PFOs has become a common procedure. Though randomized study results for its utility are pending, anecdotally it appears that closing a PFO may reduce the risk of recurrent transient ischemic attacks or stroke. In addition, there may be some benefit in treating migraine headaches.

All of the devices used in percutaneous PFO closure share the common feature that for deployment they require left atrial access through the PFO from the right atrium. Routinely, the right atrium is accessed with a catheter through the right femoral vein approach. A catheter, such as a diagnostic catheter, is a tubular structure that is designed to be advanced to various cardiovascular structures, containing a lumen that allows for measurement of pressure, allowing the delivery or removal of a fluid or providing a conduit for a wire. The catheters generally have a preformed distal shape which facilitates access to the desired location. Examples of various preformed catheters used in various other procedures besides percutaneous PFO closure are disclosed in U.S. Pat. Nos. 3,485,234, 5,885,247 and 6,004,280. Standard diagnostic multipurpose catheters are most commonly used for the percutaneous PFO closure procedure, which can usually be accomplished with routine manipulation of the catheter. However, on occasion, the manipulation of the standard multipurpose diagnostic catheter is difficult and can add significant time and risk to the procedure.

Currently there are no catheters designed for the specific purpose of percutaneous PFO closure or for delivering PFO closure devices to the PFO or for other procedures involving access to the left atrium through the PFO. There are transseptal systems for left atrial access, where the transseptal approach is described in Mullins, "Transseptal Left Heart Catheterization: Experience With a New Technique in 520 Pediatric and Adult Patients," *Pediatric Cardiology*, 4:239-246, 1983. The devices used in the transseptal approach are designed to puncture the septum and do not pinpoint the appropriate location for a PFO closure device.

The PFO catheter of the present invention overcomes the problems of the prior devices and is well-suited for an efficient percutaneous procedure relating to accessing the left atrium from the right atrium through the PFO, and especially for a PFO closure procedure, while minimizing the risks inherent in such procedures. The catheter facilitates the use of devices used in procedures involving the left atrium where access is gained to the left atrium from the right atrium through the PFO, and particularly a PFO closure procedure using PFO closure devices.

DEFINITIONS

As used herein, the singular forms "a", "an", and "the" include plural referents, and plural forms include the singular referent unless the context clearly dictates otherwise.

As used herein, the term "about" with respect to any numerical value, means that the numerical value has some reasonable leeway and is not critical to the function or operation of the component or portion of the catheter being described or the method with which the catheter is used, and will include values within plus or minus 5% of the stated value.

As used herein, the term "generally" or derivatives thereof with respect to any element, portion or parameter, means that the element, portion or parameter has the basic shape, or the parameter has the same basic direction, orientation or the like to the extent that the function of the element, portion or parameter would not be materially adversely affected by somewhat of a change in the element, portion or parameter. By way of example and not limitation, any segments of the tube that are referred to as "generally straight" refers not only to an absolutely straight segment or section, but also to such segments that may be somewhat slightly curved, so long as the curvature of the segment does not adversely affect the use of the catheter in accessing the left atrium from the right atrium through the PFO. Similarly, an element or portion of the catheter that may be described as "generally planar" to another element or portion can be oriented a few degrees more or less than exactly perfectly parallel or 0° with respect to the first element or portion, where such variations do not materially adversely affect the function of the catheter in accessing the left atrium from the right atrium through the PFO.

As used herein, the term "substantially" with respect to any numerical value or description of any element, portion or parameter means precisely the value or description of the element, portion or parameter but within reasonable industrial or medical manufacturing tolerances that would not adversely affect the function of the element, portion or parameter or the catheter containing it, but such that variations due to such reasonable industrial or medical manufacturing tolerances are less than variations described as being "about" or "generally."

BRIEF SUMMARY OF THE INVENTION

A first aspect of the present invention relates to a catheter having a preformed shape for use in accessing a left atrium of a living heart within a subject's body by passing from the heart's right atrium to the heart's left atrium through a patent foramen ovale in the heart, the catheter comprising a tube of a length sufficient to extend out of the body containing the heart, the tube having a lumen of a sufficient diameter adapted to accommodate a wire within the lumen, the catheter having a proximal end portion terminating at a proximal opening, the catheter further having a distal end portion terminating at a distal opening, the proximal end portion being extendable from the subject's body when the distal end portion is at least partially within the subject's heart, and the catheter further comprising a primary curve and a secondary curve between the proximal end portion and the distal opening, the primary curve having a beginning curvature point and an end curvature point of the primary curve, the secondary curve having a having an initial curvature point and a final curvature point, and the catheter having an intermediate segment between the end curvature point of the primary curve and the beginning curvature point of the secondary curve and an distal segment between the final curvature point of the secondary curve and the distal opening; wherein:

the beginning curvature point of the primary curve is located about 4 cm to about 9 cm from the distal opening, the primary curve being oriented in a first direction and having a radius of curvature of about 2 cm to about 4 cm;

the secondary curve is located at the distal end portion with an initial curvature point beginning about 0.25 cm to about 2 cm from the distal opening, the secondary curve being oriented in a second direction opposite the first direction of the primary curve and having a radius of curvature of about 0.1 cm to about 0.4 cm;

the catheter having a projected longitudinal distance from the beginning curvature point of the primary curve to the initial curvature point of the secondary curve of about 3 cm to about 6 cm;

the catheter having a projected lateral distance from the beginning curvature point of the primary curve to the initial curvature point of the secondary curve of about 2 cm to about 6 cm; and the catheter having a projected longitudinal distance from the initial curvature point of the secondary curve to the distal opening of about 0.2 cm to about 2 cm.

Another aspect of the present invention is a method of using the catheter of the invention in accessing a left atrium of a living heart within a subject's body by passing from the heart's right atrium to the heart's left atrium through a patent foramen ovale in the heart. The method comprises:

a. providing a catheter as set forth above concerning the first aspect of the present invention;

b. passing, with imaging guidance, from the subject's femoral vein to the subject's heart's superior vena cava, the catheter alone or the catheter over a guide wire within the catheter's lumen when the guide wire has previously been inserted from the subject's femoral vein to the subject's heart's superior vena cava;

c. positioning, with imaging guidance, the catheter by manipulating the catheter until the distal opening of the catheter engages the fossa ovalis in the subject's heart's right atrium;

d. locating, with imaging guidance, the distal opening of the catheter in the subject's heart's patent foramen ovale canal; and e. advancing, with imaging guidance, the catheter's distal opening by manipulating the catheter itself, or by advancing the guide wire within the lumen of the catheter, into the subject's heart's left atrium.

The catheter of the invention provides easy access to the left atrium through the PFO, since the catheter is specifically designed for this purpose by virtue of the unique preformed curves and other structural components, including the dimensions thereof, that direct the catheter to and through the PFO.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

DETAILED DESCRIPTION OF THE PREFERRED EMBODIMENTS

Figure 1:
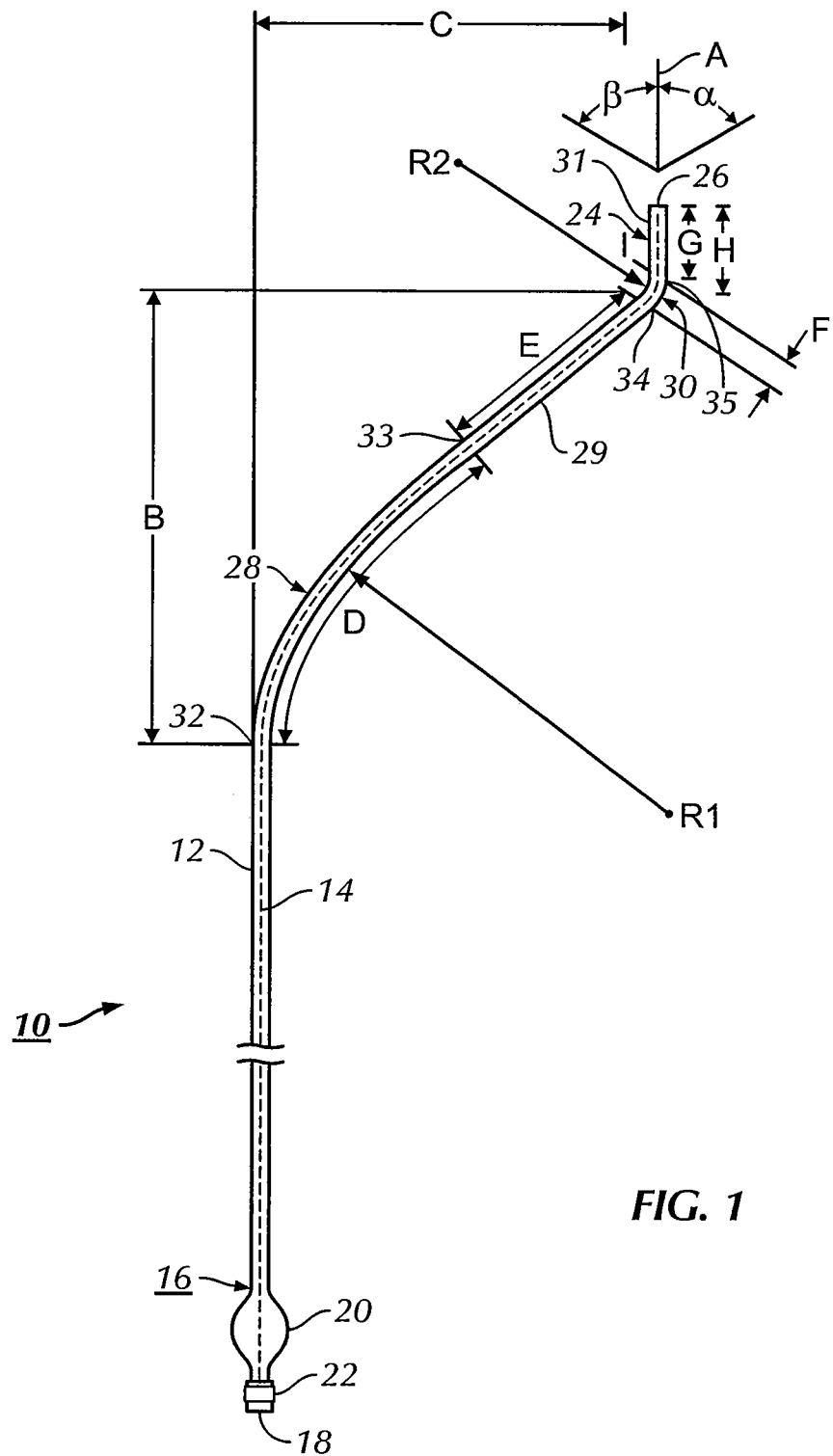
FIG. 1 is a schematic representation, in a side elevation view, of one embodiment of a catheter according to the present invention.

As shown in detail in FIG. 1, the catheter 10 of the present invention comprises a tube 12 with a lumen 14 illustrated by a dashed line. The catheter 10 has a proximal end portion 16 terminating at a proximal opening 18, adjacent a hub 20. The proximal end of the hub includes an appropriate connector, such as a Luer connector 22, for connection to a syringe or a manifold or the like to a source of liquid used in the desired procedure, such as a PFO closure procedure. The catheter 10 also has a distal end portion 24 terminating at a distal opening 26. The lumen 14 extends within the tube 12 between the proximal opening 18 and the distal opening 26.

If desired, a suitable portion of the catheter adjacent the distal opening 26 may include a suitable marker to render the distal end 24, particularly immediately adjacent the distal opening 26, easier to locate and its position easier to monitor while inserting the catheter into and through the desired locations within the subject's body. The insertion and movement are typically monitored with appropriate imaging, including, but not limited to ultrasound, fluoroscopy, magnetic resonance (MRI) scanning or computed axial tomography, sometimes referred to as computed tomography (CT) scanning.

Figure 2:
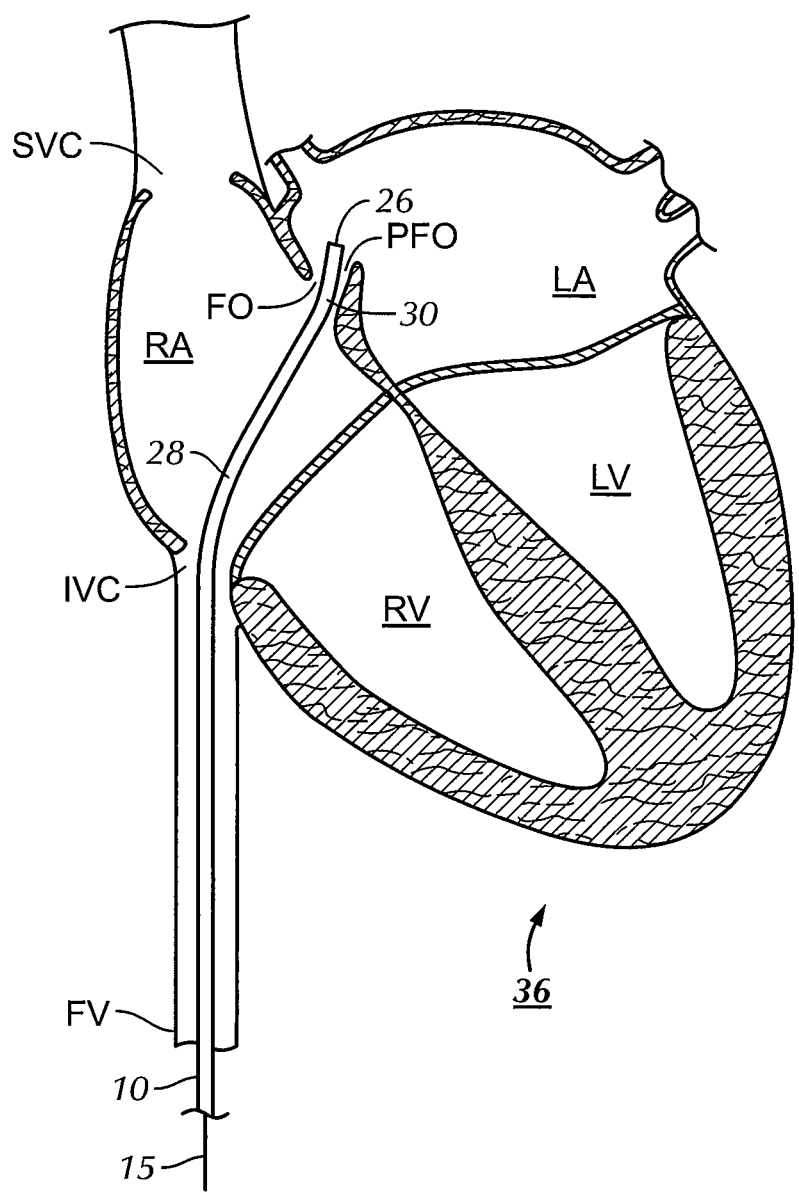
FIG. 2 is a schematic representation, in a side elevation view, depicting the use of the embodiment of the catheter of the invention shown in FIG. 1 in a method according to the present invention of preparing to percutaneously close a patent foramen ovale in a living heart within a subject's body.

The length of the catheter 10 is sufficient to extend out of the body of the subject undergoing the procedure from or involving access to the left atrium through the PFO, such as the PFO closure procedure, which usually commences by inserting the catheter through and entry port in the subject's femoral vein FV, but can be used in any vein that communicates with the right atrium RA (shown in FIG. 2). As such, the catheter may be any suitable length, such as about 60 cm to about 120 cm, and preferably about 100 cm. The diameter of the catheter can be any suitable diameter, typically about 4 French to about 8 French (where 1 French is 0.33 mm). The lumen 14 allows passage of fluids, and passage of a guide wire 15 (shown in FIG. 2), used to guide the catheter and sheaths containing other devices used in procedures involving access to the left atrium through the PFO, such as, without limitation, PFO closure devices, to the area of treatment. Typically, a guide wire has a diameter of ranging from about 0.035 cm to about 0.097 cm. The lumen 14 also allows pressure measurements to be taken when a pressure gauge is attached to or in pressure communication with the proximal opening 18.

The catheter is made of material that can be preformed into the desired shape to be described hereinafter, such that the preformed shape is maintained when the catheter is not subject to a stress or force, such as may be the case when it is inserted into a sheath (not shown) for insertion into a subject's blood vessel or the like, for instance the femoral vein FV. Thus, the material used for the catheter must be sufficiently stiff to be able to be advanced within blood vessels and other anatomic structures when within the subject's body, but is still sufficiently flexible to bend within the subject's anatomy, with a memory to return to the preformed shape when the catheter 10 is removed from a sheath or other confining structure. The particular materials used to make the catheter 10 do not form a part of this invention, since they are conventional biocompatible materials, such as medical grade polyvinylchloride, nylons and polyamides, including polyamide materials which are copolymers and include structural components in addition to amide groups, or other suitable synthetic polymer typically used to make preformed catheters. Also typically, the catheter 10 may include reinforcing metal, braiding or other materials as is known to those skilled in the art, and using the extrusion, molding, thermoforming or other suitable techniques also known to those skilled in the art. A catheter 10 of the present invention may be made using the materials and techniques as described in U.S. Pat. No. 3,485,234, the entire disclosure of which is hereby incorporated by reference herein.

The catheter 10 includes a generally straight portion extending from the proximal end portion 16 for approximately the proximal two thirds or more of its length. While FIG. 1 indicates that the distal end portion 24 of the catheter 10 is immediately adjacent the distal opening 26, the distal end portion 24 actually includes the entire portion of the catheter 10 starting at a beginning curvature point 32 of a primary curve 28 to the distal opening 26. Thus, at the distal end portion 24 of the catheter 10, the catheter includes at least two curves, a primary curve 28 oriented in a first direction and a secondary curve 30 oriented in a second direction opposite the first direction of the primary curve 28, where the second direction may be generally coplanar with respect to the plane of the catheter 10 and the first curve, although as explained below regarding certain other embodiments, the secondary curve 30 also could be angled in a third direction. The primary curve 28 facilitates the distal opening 26 engaging the fossa ovalis FO (shown in FIG. 2). When the catheter 10 is in the anatomically correct position such that the distal end portion 24 is in the heart, the secondary curve 30 turns superiorly and directs the distal opening 26 of the catheter 10 into the PFO canal (labeled as "PFO" in FIG. 2).

An intermediate segment 29 of the tube 12 extends between the primary curve 28 and the secondary curve 30, and a distal segment 31 of the tube extends between the secondary curve and the distal opening 26. The intermediate segment 29 and the distal segment 31 are unitarily and integrally formed with the tube 12, and are preferably generally straight portions of the tube 12, but may also be somewhat curved, so long as any curvature of the intermediate segment 29 or the distal segment 31 does not adversely affect the function of the catheter in a PFO closure procedure using the catheter 10.

The following points along the length of the catheter 10 from the proximal end portion 16 to the distal opening 26 as shown in FIG. 1 are used to describe and explain the catheter. The primary curve begins at a beginning curvature point 32 and ends at an end curvature point 33, and has an arc length D. The end curvature point 33 of the primary curve also marks the beginning of the intermediate segment 29. The secondary curve 30 starts at an initial curvature point 34, which also marks the end of the intermediate segment, which has a length E. The secondary curve has an arc length F from the initial curvature point 34 to the final curvature point 35, which also marks the start of the distal segment 31. The distal segment extends to the end of the catheter 10 at the distal opening 26, and has a length G.

So that the PFO catheter 10 of the present invention is most useful for accessing the left atrium from the right atrium through the PFO, for procedures including but not limited to a PFO closure procedure, the catheter 10 has certain generally and preferably substantially particularly defined dimensions for its various portions, curves with the indicated radii of curvatures and other relationships of the portions of the catheter to each other. Among the basic relationships that are important, but bearing in mind that hearts of subjects, including human subjects, are of different sizes, depending on the individual and the individual's age, are three projections of combined portions of the catheter 10, such that the catheter 10 is useful in its intended procedure.

The catheter 10 has a projected longitudinal distance B from the beginning point of curvature 32 of the primary curve 28 to the initial curvature point 34 of the secondary curve 30, broadly of about and preferably substantially 3 cm to about and preferably substantially 6 cm; preferably about and preferably substantially 3 cm to about and preferably substantially 5 cm; and more preferably about and preferably substantially 3.5 cm.

The catheter 10 has a projected lateral distance C from the beginning curvature point 32 of the primary curve 28 to the initial curvature point 34 of the secondary curve 30, broadly of about and preferably substantially 2 cm to about and preferably substantially 6 cm; preferably about and preferably substantially 2 cm to about and preferably substantially 5 cm; and more preferably about and preferably substantially 2.5 cm.

The catheter 10 has a projected longitudinal distance H from the initial curvature point 34 of the secondary curve 30 to the distal opening 26, broadly of about and preferably substantially 0.2 cm to about and preferably substantially 2 cm; preferably about and preferably substantially 0.3 cm to about and preferably substantially 1 cm; and more preferably about and preferably substantially 0.5 cm.

Since the usefulness of the PFO catheter 10 of the present invention is dependent on the procedures used in or involving access to the left atrium from the right atrium through the PFO, such as to effect the closure of the PFO, the important dimensions and relations of the components or portions of the catheter 10 are determined from the distal opening 26, as the tools and materials used in such procedures must be positioned properly and moved efficiently into place in the left atrium through the PFO as shown in FIG. 2. Therefore, the distances of the portions are best measured from the distal opening 26.

Based on the more preferred dimensions set forth below, the arc length D of the primary curve 28 is about and preferably substantially 52.1% of the distance between the beginning curvature point 32 of the primary curve 28 to the distal opening 26; the length E of the intermediate segment 29 is about and preferably substantially 37.3% of the distance between the beginning curvature point 32 of the primary curve 28 to the distal opening 26; the arc length F of the secondary curve 30 is about and preferably substantially 4.4% of the distance between the beginning curvature point 32 of the primary curve 28 to the distal opening 26; and the length G of the distal segment 31 is about and preferably substantially 6.2% of the distance between the beginning curvature point 32 of the primary curve 28 to the distal opening 26.

After the generally straight proximal portion of the catheter 10, the distal end portion 24 begins at and the primary curve 28 is oriented in a first direction that starts at the beginning curvature point 32 located broadly about and preferably substantially 4 cm to about and preferably substantially 9 cm, and preferably about and preferably substantially 4 cm to about and preferably substantially 7 cm, from the distal opening 26 and ending at the end curvature point 33 where the primary curve joins the intermediate segment 29. More preferably, the beginning curvature point 32 is located about and preferably substantially 4.5 cm to about and preferably substantially 6 cm from the distal opening 26. Even more preferably, the beginning curvature point 32 is located about and preferably substantially 5 cm from the distal opening 26.

The primary curve 28 has a shape in the form of an arc having a radius of curvature R1, broadly of about and preferably substantially 2 cm to about and preferably substantially 4 cm; preferably about and preferably substantially 2.5 cm to about and preferably substantially 3.5 cm; and more preferably about and preferably substantially 3 cm. The primary curve 28 has an arc length D, broadly of about and preferably substantially 2.1 cm to about and preferably substantially 3.65 cm; preferably about and preferably substantially 2.3 cm to about 3.1 cm; and more preferably about and preferably substantially 2.61 cm.

The intermediate segment 29 has a length E, broadly of about and preferably substantially 1.5 cm to about and preferably substantially 2.6 cm; preferably about and preferably substantially 1.7 cm top about and preferably substantially 2.2 cm; and more preferably about 1.87 cm.

The secondary curve 30 is oriented in a second direction opposite the first direction of the primary curve and starts at the initial curvature point 34 about and preferably substantially 0.25 cm to about and preferably substantially 2 cm from the distal opening 26.

Preferably, the initial curvature point 34 of the secondary curve 30 is about 0.5 cm to about 1.5 cm from the distal opening 26, and more preferably about 1 cm from the distal opening 26. The secondary curve 30 has a radius of curvature R2, broadly of about and preferably substantially 0.1 cm to about 0.4 cm; preferably about and preferably substantially 0.2 cm to about 0.3 cm; and more preferably about and preferably substantially 0.25 cm. The secondary curve 30 has an arc length F, broadly of about and preferably substantially 0.18 cm to about and preferably substantially 0.31 cm; preferably about and preferably substantially 0.20 cm to about 0.26 cm; and more preferably about and preferably substantially 0.22 cm.

While the secondary curve 30 can be and preferably is located in the same plane as the rest of the tube 12 and primary curve 28 of the catheter 10, represented by the plane of the paper of the sheet containing FIG. 1, so as to be generally planar with respect to the primary curve, the secondary curve 30 may be located to be out of the plane of the plane of the primary curve 28, providing the catheter 10 with a three dimensional shape. Thus, the secondary curve 30 may be angled from the plane of the primary curve 28 at the initial curvature point 34 of the secondary curve 30 in a third direction. When the secondary curve 30 is moved out of the plane of the primary curve 28, the secondary curve 30 may be out of the plane of the primary curve 28 along an axis A representative of the tube 12 proximal to the initial curvature point 34 of the secondary curve 30 by an angle α of about 60° (illustrated in FIG. 1 as being a positive angle extending above the plane of the paper, assumed for purposes of illustration as the plane of the rest of the catheter 10 and the primary curve 28) to an angle β of about −60° (illustrated in FIG. 1 as being a negative angle extending below the plane of the paper), such that the angle compared to the plane of the primary curve 28 is ±60°. Preferably, where an angled secondary curve is desired, angle α is about 30° or angle β is −30°, such that the angle of the secondary curve 30 in the second direction compared to the plane of the primary curve 28 is ±30°. More preferably, where an angled secondary curve is desired, angle α is 15° or angle β is −15°, such that the angle compared to the plane of the primary curve 28 is ±15°. The choice of the angle, if any, for the secondary curve 30 would be determined by the specific cardiac anatomy which is assessed with various imaging techniques including but not limited to, ultrasound, fluoroscopy, MRI scanning or CT scanning.

The distal segment 31 begins at the final curvature point 35 of the secondary curve 30 and ending at the distal opening, with a length G, broadly of about and preferably substantially 0.25 to about and preferably substantially 1.8 cm. Preferably, the length G of the distal segment 31 is about and preferably substantially 0.25 cm to about and preferably substantially 0.43 cm; more preferably about and preferably substantially 0.28 to about and preferably substantially 0.37 cm; and even more preferably about and preferably substantially 0.31 cm.

As noted above, the present invention also includes a method of accessing a left atrium of a living heart within a subject's body by passing from the heart's right atrium to the heart's left atrium through a patent foramen ovale in the heart using the catheter 10 of the present invention. This is done for various procedures where access to the left atrium is required or desirable, such as, without limitation, various left atrium ablation procedures and preferably to prepare to percutaneously close a patent foramen ovale in a living heart within a subject's body. More specifically, the catheter 10 is used as follows in this method, with reference to FIG. 2, schematically illustrating the final position of the catheter where the distal opening 26 is located in the PFO canal extending to the left atrium. In the schematic representation of the anatomy of the subject in FIG. 2, FA designates the femoral artery, IVC designates the inferior vena cava, RA designates the right atrium, RV designates the right ventricle, SVC designates the superior vena cava, FO designates the fossa ovalis, PFO designates the patent foramen ovale canal, LA designates the left atrium and LV designates the left ventricle.

The catheter 10 is advanced, with imaging guidance, through an appropriate vein, typically the femoral vein, and usually through a sheath already in the vein with a homeostasis valve. The catheter 10 is typically, but not necessarily advanced over a guide wire 15 in the lumen 14 of the catheter 10. Under imaging guidance, the catheter is passed to the inferior vena cava IVC, the right atrium RA and the superior vena cava SVC. If desired, the catheter 10 may contact the junction of the inferior vena cava IVC and the right atrium RA, for example without limitation, by moving the catheter 10 slightly to the left as shown in FIG. 2, for support of the catheter when it is being positioned in the heart. The guide wire, when used, may then be removed, allowing the catheter 10 to assume the preformed shape due to the memory of the materials used to form the catheter. The catheter 10 is rotated medially and pulled inferiorly into the right atrium RA. This process directs the catheter's distal opening 26 to the fossa ovalis FO. Under imaging guidance, the distal opening 26 is maneuvered into the PFO canal. The guide wire can be re-advanced through the catheter into the PFO canal to the left atrium LA. Having placed the guide wire into position in the left atrium LA through the PFO canal, the catheter may be withdraw and a sheath containing appropriate devices for the intended procedure may be slid over the guide wire into position in the left atrium LA through the PFO canal. Once the devices are in position, the procedure to be performed from the left atrium LA, such as a PFO closure procedure, may be performed.

An experimental PFO catheter 10 of the present invention was made using a heat gun to shape a standard, U.S. Food and Drug Administration-approved multipurpose catheter. The experimental PFO catheter had the most preferred dimensions and radii of curvature as described above, and the secondary curve 30 was in the plane of the primary curve 28. Using this experimental PFO catheter, three experimental PFO closure procedures were performed on human patients. Crossing of the PFO canal took less than three minutes for all three cases. In typical PFO closure procedures using the standard multipurpose catheters, the average time to cross the PFO canal is about five minutes, but the time can and sometimes does take 30 or more minutes. When involved in this type of PFO closure procedure, it is important that the positioning of the catheter distal opening 26 be accomplished as quickly as possible while being careful when the distal end portion 24 is within the subject's body. A savings of two minutes in a catheterization procedure that usually takes at least five minutes is a significant advantage of the PFO catheter of the present invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A catheter having a preformed shape for accessing a left atrium of a living heart within a subject's body by passing from the heart's right atrium to the heart's left atrium through a patent foramen ovale in the heart, the catheter comprising a tube of a length of about 60 cm to about 120 cm to extend out of the body containing the heart, the tube having a lumen of a diameter of about 4 French to about 8 French adapted to accommodate a wire within the lumen, the catheter having a proximal end portion terminating at a proximal opening, the catheter further having a distal end portion terminating at a distal opening, the proximal end portion being extendable from the subject's body when the distal end portion is at least partially within the subject's heart, and the catheter further comprising a primary curve and a secondary curve between the proximal end portion and the distal opening, the primary curve having a beginning curvature point and an end curvature point of the primary curve, the secondary curve having an initial curvature point and a final curvature point, and the catheter having an intermediate segment between the end curvature point of the primary curve and the initial curvature point of the secondary curve and a distal segment between the final curvature point of the secondary curve and the distal opening; wherein:

the beginning curvature point of the primary curve is located about 4 cm to about 9 cm from the distal opening, the primary curve being oriented in a first direction and having a radius of curvature of about 2 cm to about 4 cm;

the secondary curve is located at the distal end portion with an initial curvature point beginning about 0.25 cm to about 2 cm from the distal opening, the secondary curve being oriented in a second direction opposite the first direction of the primary curve and having a radius of curvature of about 0.1 cm to about 0.4 cm;

the catheter having a projected longitudinal distance from the beginning curvature point of the primary curve to the initial curvature point of the secondary curve of about 3 cm to about 6 cm;

the catheter having a projected lateral distance from the beginning curvature point of the primary curve to the initial curvature point of the secondary curve of about 2 cm to about 6 cm; and the catheter having a projected longitudinal distance from the initial curvature point of the secondary curve to the distal opening of about 0.2 cm to about 2 cm.

2. The catheter of claim 1, wherein the beginning curvature point of the primary curve is located about 4 cm to about 7 cm from the distal opening, and the initial curvature point of the secondary curve is located about 0.25 cm to about 1 cm from the distal opening.

3. The catheter of claim 2, wherein the beginning curvature point of the primary curve is located about 4.5 cm to about 6 cm from the distal opening, and the initial curvature point of the secondary curve is located about 0.4 cm to about 0.8 cm from the distal opening.

4. The catheter of claim 3, wherein the beginning curvature point of the primary curve is located about 5 cm from the distal opening, and the initial curvature point of the secondary curve is located about 0.5 cm from the distal opening.

5. The catheter of claim 2, wherein the primary curve has an arc length of about 52.1% of the distance from the beginning curvature point of the primary curve to the distal opening, the intermediate segment has a length of about 37.3% of the distance from the beginning curvature point of the primary curve to the distal opening, the secondary curve has an arc length of about 4% of the distance from the beginning curvature point of the primary curve to the distal opening, and the distal segment has a length of about 6.2% of the distance from the beginning curvature point of the primary curve to the distal opening.

6. The catheter of claim 2, wherein the primary curve has an arc length of about 2.1 cm to about 3.65 cm, the intermediate segment has a length of about 1.5 cm to about 2.6 cm, the secondary curve has an arc length of about 0.18 cm to about 0.31 cm, and the distal segment has a length of about 0.25 cm to about 0.43 cm; and wherein the projected longitudinal distance from the beginning point of curvature of the primary curve to the initial curvature point of the secondary curve is about 3 cm to about 5 cm, the projected lateral distance from the beginning point of the primary curve to the initial curvature point of the secondary curve is about 2 cm to about 5 cm, and the projected longitudinal distance from the initial curvature point of the secondary curve to the distal opening is about 0.25 cm to about 1 cm.

7. The catheter of claim 6, wherein the primary curve has an arc length of about 2.3 cm to about 3.1 cm, the intermediate segment has a length of about 1.7 cm to about 2.2 cm, the secondary curve has an arc length of about 0.2 cm to about 0.26 cm, and the distal segment has a length of about 0.28 cm to about 0.37 cm; and wherein the primary curve has a radius of curvature of about 2.5 cm to about 3.5 cm and the secondary curve has a radius of curvature of about 0.2 cm to about 0.3 cm.

8. The catheter of claim 7, wherein the primary curve has an arc length of about 2.61 cm, the intermediate segment has a length of about 1.87 cm, the secondary curve has an arc length of about 0.22 cm, and the distal segment has a length of about 0.31 cm;
   wherein the primary curve has a radius of curvature of about 3 cm and the secondary curve has a radius of curvature of about 0.25 cm; and
   wherein the projected longitudinal distance from the beginning point of curvature of the primary curve to the initial curvature point of the secondary curve is about 3.5 cm, the projected lateral distance from the beginning point of the primary curve to the initial curvature point of the secondary curve is about 2.5 cm, and the projected longitudinal distance from the initial curvature point of the secondary curve to the distal opening is about 0.5 cm.

9. The catheter of claim 2, wherein the catheter tube has a plane that includes the primary curve, and the secondary curve is angled from the plane of the primary curve at the initial curvature point of the secondary curve in a third direction at an angle of about ±30° from the plane of the primary curve.

10. The catheter of claim 9, wherein the angle of the secondary curve in the third direction is an angle of about ±15° from the plane of the primary curve.

11. The catheter of claim 1, wherein the catheter tube has a plane that includes the primary curve, and the secondary curve is angled from the plane of the primary curve at the initial curvature point of the secondary curve in a third direction, measured from the plane of the primary curve.

12. The catheter of claim 11, wherein angle of the secondary curve in the third direction is an angle of about ±60° from the plane of the primary curve.

13. A method of accessing a left atrium of a living heart within a subject's body by passing from the heart's right atrium to the heart's left atrium through a patent foramen ovale in the heart, the method comprising:
   a. providing a catheter according to claim 1;
   b. passing, with imaging guidance, from the subject's femoral vein to the subject's heart's superior vena cava, the catheter alone or the catheter over a guide wire within the catheter's lumen when the guide wire has previously been inserted from the subject's femoral vein to the subject's heart's superior vena cava;
   c. positioning, with imaging guidance, the catheter by manipulating the catheter until the distal opening of the catheter engages the fossa ovalis in the subject's heart's right atrium;
   d. locating, with imaging guidance, the distal opening of the catheter in the subject's heart's patent foramen ovale canal; and
   e. advancing, with imaging guidance, the catheter's distal opening by manipulating the catheter itself, or by advancing the guide wire within the lumen of the catheter, into the subject's heart's left atrium.

14. The method of claim 13, wherein the b. positioning includes rotating the catheter medially and pulling the catheter inferiorly into the right atrium.

15. The method of claim 13, wherein the beginning curvature point of the primary curve is located about 4 cm to about 7 cm from the distal opening, and the initial curvature point of the secondary curve is located about 0.25 cm to about 1 cm from the distal opening.

16. The method of claim 15, wherein the catheter tube has a plane that includes the primary curve, and the secondary curve is angled from the plane of the primary curve at the initial curvature point of the secondary curve in a third direction at an angle of about ±30° from the plane of the primary curve.

17. The catheter of claim 16, wherein the angle of the secondary curve in the third direction is an angle of about ±15° from the plane of the primary curve.

18. The method of claim 13, wherein the beginning curvature point of the primary curve is located about 4.5 cm to about 6 cm from the distal opening, and the initial curvature point of the secondary curve is located about 0.4 cm to about 0.8 cm from the distal opening.

19. The method of claim 13, wherein the beginning curvature point of the primary curve is located about 5 cm from the distal opening, and the initial curvature point of the secondary curve is located about 0.5 cm from the distal opening.

20. The method of claim 13, wherein the primary curve has an arc length of about 52.1% of the distance from the beginning curvature point of the primary curve to the distal opening, the intermediate segment has a length of about 37.3% of the distance from the beginning curvature point of the primary curve to the distal opening, the secondary curve has an arc length of about 4% of the distance from the beginning curvature point of the primary curve to the distal opening, and the distal segment has a length of about 6.2% of the distance from the beginning curvature point of the primary curve to the distal opening.

21. The method of claim 13, wherein the primary curve has an arc length of about 2.1 cm to about 3.65 cm, the intermediate segment has a length of about 1.5 cm to about 2.6 cm, the secondary curve has an arc length of about 0.18 cm to about 0.31 cm, and the distal segment has a length of about 0.25 cm to about 0.43 cm; and
   wherein the projected longitudinal distance from the beginning point of curvature of the primary curve to the initial curvature point of the secondary curve is about 3 cm to about 5 cm, the projected lateral distance from the beginning point of the primary curve to the initial curvature point of the secondary curve is about 2 cm to about 5 cm, and the projected longitudinal distance from the initial curvature point of the secondary curve to the distal opening is about 0.25 cm to about 1 cm.

22. The method of claim 13, wherein the primary curve has an arc length of about 2.3 cm to about 3.1 cm, the intermediate segment has a length of about 1.7 cm to about 2.2 cm, the secondary curve has an arc length of about 0.2 cm to about 0.26 cm, and the distal segment has a length of about 0.28 cm to about 0.37 cm; and
   wherein the primary curve has a radius of curvature of about 2.5 cm to about 3.5 cm and the secondary curve has a radius of curvature of about 0.2 cm to about 0.3 cm.

23. The method of claim 13, wherein the primary curve has an arc length of about 2.61 cm, the intermediate segment has a length of about 1.87 cm, the secondary curve has an arc length of about 0.22 cm, and the distal segment has a length of about 0.31 cm;
   wherein the primary curve has a radius of curvature of about 3 cm and the secondary curve has a radius of curvature of about 0.25 cm; and
   wherein the projected longitudinal distance from the beginning point of curvature of the primary curve to the initial curvature point of the secondary curve is about 3.5 cm, the projected lateral distance from the beginning point of the primary curve to the initial curvature point of the secondary curve is about 2.5 cm, and the projected longitudinal distance from the initial curvature point of the secondary curve to the distal opening is about 0.5 cm.

24. The method of claim 13, wherein the catheter tube has a plane that includes the primary curve, and the secondary curve is angled from the plane of the primary curve at the initial curvature point of the secondary curve in a third direction, measured from the plane of the primary curve.

25. The method of claim 24, wherein angle of the secondary curve in the third direction is an angle of about ±60° from the plane of the primary curve.

\* \* \* \* \*